United States Patent [19]
Boussignac et al.

[11] Patent Number: 6,056,767
[45] Date of Patent: May 2, 2000

[54] SYSTEM FOR THE TREATMENT OF A BODY DUCT AND PROCESS FOR ITS MANUFACTURE

[75] Inventors: Georges Boussignac, Antony; Viviane Payrou, Fresnes, both of France

[73] Assignee: Laboratoires Nycomed S.A., Paris, France

[21] Appl. No.: 09/151,326

[22] Filed: Sep. 11, 1998

[30] Foreign Application Priority Data

Sep. 12, 1997 [FR] France .................................. 97 11364

[51] Int. Cl.⁷ .................................................. A61M 29/00
[52] U.S. Cl. .............................. 606/194; 606/198; 623/1; 623/12
[58] Field of Search ................................ 606/1, 108, 192, 606/193, 194, 198, 200; 623/1, 12

[56] References Cited

U.S. PATENT DOCUMENTS

| | | |
|---|---|---|
| 4,886,062 | 12/1989 | Wiktor . |
| 5,147,302 | 9/1992 | Euteneuer et al. . |
| 5,383,928 | 1/1995 | Scott et al. . |
| 5,507,770 | 4/1996 | Turk . |
| 5,665,117 | 9/1997 | Rhodes . |
| 5,792,172 | 8/1998 | Fischell et al. ........................ 606/198 |
| 5,814,061 | 9/1998 | Osborne et al. ....................... 606/198 |

*Primary Examiner*—Michael Buiz
*Assistant Examiner*—William Lewis
*Attorney, Agent, or Firm*—Merchant & Gould P.C.

[57] ABSTRACT

The object of the present invention is a system for the treatment of a body duct, such as a blood vessel in particular, of the type comprising a stent forming element comprising a frame made from a material having a low elastic recovery capacity, which is intended, in the position of use, to restore and/or to maintain the normal passage cross-section of said duct to be treated, and an inflatable expanding element disposed in the interior relative to said stent forming element.

13 Claims, 2 Drawing Sheets

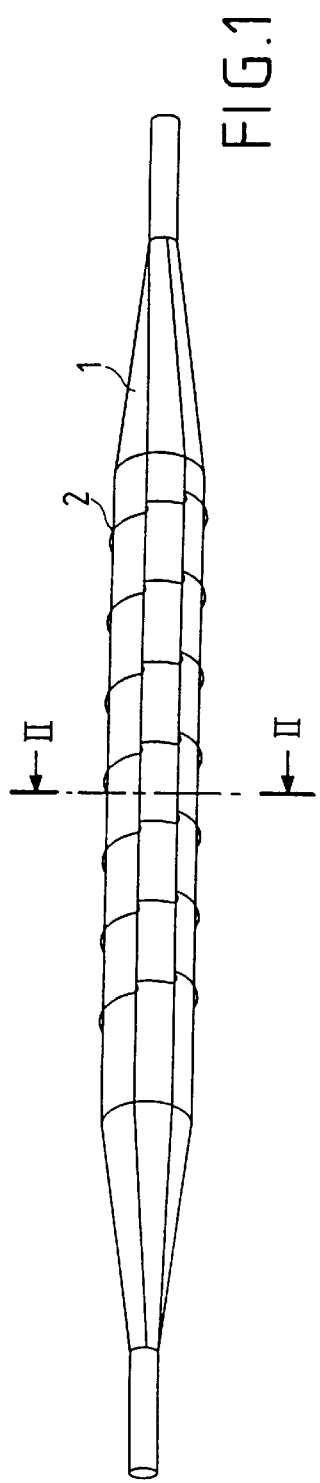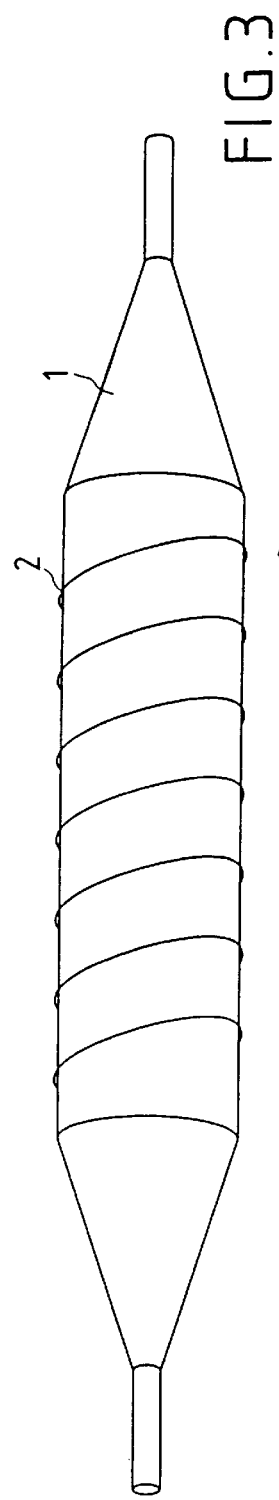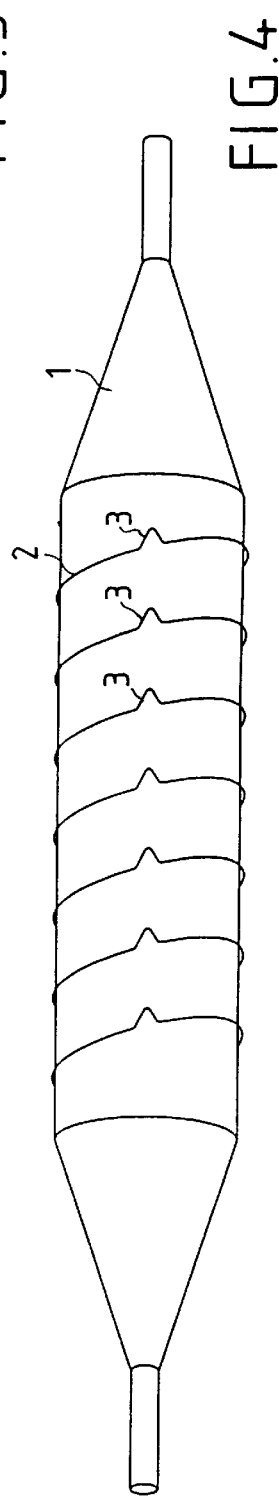

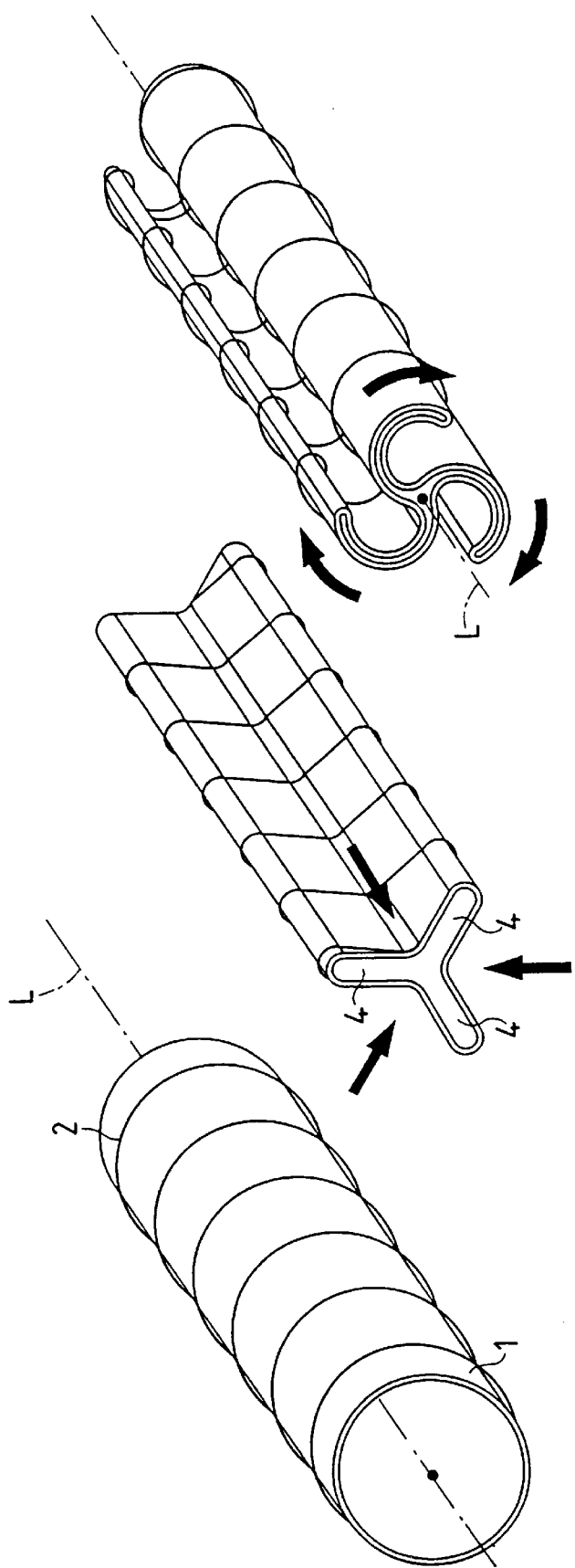

SYSTEM FOR THE TREATMENT OF A BODY DUCT AND PROCESS FOR ITS MANUFACTURE

BACKGROUND OF THE INVENTION

1. Field of the Invention

The present invention relates in general terms to a system for the treatment of a body duct and process for its manufacture.

The invention applies mainly to the field of treatment of blood vessels having stenoses or aneurysms and more generally to the field of the treatment of various anatomical ducts of the human or animal body, such as, for example, the urinary ducts and especially the urethra, the digestive ducts and especially the oesophagus, or even the respiratory ducts and especially the trachea.

2. Description of the Related Art

The narrowing of the body ducts and especially the blood ducts (vessels, arteries or veins) are the origin of serious disorders, and various techniques have been developed to prevent such complaints.

Within the context of the treatment of a stenotic blood vessel, the conventional technique, referred to as angioplasty, concerns the use of a dilatation catheter, which has on its distal extremity an inflatable expanding element, referred to as a balloon or balloon-tip. This dilatation catheter is introduced into the interior of the artery, and when the balloon is positioned at the level of the stenosis, the balloon is then inflated to a relatively high pressure, in such a way as to compress the stenosis in the wall of the artery and to thus restore the normal passage cross-section of said artery at the location of the stenosis.

More and more, this conventional angioplasty technique is accompanied or completed by the percutaneous implantation, in the interior of the stenotic vessel, a device, commonly designated by the American term "stent", for preventing the dilated vessel from spontaneously closing up again or for preventing its occlusion by the formation of a new atheromatous plaque and the possible recurrence of stenosis.

Stents are generally divided into two major categories.

So-called auto-expandable stents are capable of changing by themselves from a first, constricted position, of reduced diameter, enabling them to be guided through the body duct, to a second, expanded working position.

These devices can be made from a material of recovery capacity, or even be shaped so as to possess an "internal elastic recovery capacity" enabling them to change from a first, constricted position under stress, to a second, expanded working position.

The second category of stents consists of devices whose expansion can be forced mechanically, generally under the effect of a force exerted from the inside outwards in a radial direction, such as, for example, the force exerted during the inflation of a balloon disposed inside said stent.

Such devices are generally made of materials with a low elastic recovery capacity which are capable of undergoing an irreversible plastic deformation.

This type of stent is currently the most commonly employed, in particular because it is easier to implant than the above-mentioned auto-expandable stents.

Hitherto, the devices belonging to this second category of stents are constituted of a tubular frame of reduced diameter of shape corresponding to the shape desired in the stressed position.

The deformation of these devices, under the effect of the inflation of the balloon, causes their radial expansion but is accompanied by a decrease in length. Such known devices in general also lack longitudinal flexibility.

Furthermore, it has been observed that the expansion of these known devices does not take place in a regular manner, their symmetry not being itself sufficient to distribute the forces of deformation acting on it during the inflation of the balloon.

The irregular expansion of these devices, due notably to the absence of distribution of the radial forces acting on it, results notably in it not being possible to obtain a passage of constant dimension in the body duct, and from this, this type of device is not entirely satisfactory.

The irregular expansion of these devices is also due to the fact that during the inflation of the balloon, the balloon has a tendency to first of all inflate at its ends, thus causing a compression of the stent in the longitudinal direction.

Finally, it has been observed in these known devices that the stent forming element is not always maintained on the balloon during the inflation and consequently risks shifting during intervention.

SUMMARY OF THE INVENTION

Under these conditions, the object of the present invention is to solve the technical problem consisting of providing a system for the treatment of a body duct, such as a blood vessel in particular, of a new design which guarantees a regular spreading out of the stent forming element during the inflation of the expanding element which acts to position it, as well as a distribution of the radial forces acting on it after positioning, and which thus enables obtaining, in a secure way, a constant passage in the body duct to be treated.

In accordance with the present invention, the solution for solving this technical problem consists of a system for the treatment of a body duct, such as a blood vessel in particular, of the type comprising:

a stent forming element comprising a frame made from a material having a low elastic recovery capacity, which is intended, in the position of use, to restore and/or to maintain the normal passage cross-section of said duct to be treated, an inflatable expanding element disposed in the interior relative to said stent forming element, characterised in that said expanding element and said stent forming element, in their structure corresponding to the position of use, are jointly folded with a winding around their longitudinal axis.

Thus, the originality of the present invention with regard to the existing state of the art, resides in the fact that the frame of the stent forming element is not constituted in the form of a tubular element of reduced diameter which can expand radially to give a larger diameter, but this frame is constituted in the form of a tubular element having a shape which corresponds to the shape desired in the position of use, said tubular element further being folded with a winding around its longitudinal axis, and then unfolded jointly with the inflatable expanding element acting to position it.

This characteristic ensures a regular spreading out of the stent forming element, guided by the expanding element, during its spreading out by inflation, by thus preventing any longitudinal compression of the stent forming element.

Moreover, the radial expansion of the stent forming element may also be obtained without decreasing the length of it.

Finally, the joint spreading out of the inflatable expanding element and the stent forming element ensures a good upkeep of said stent forming element which does not therefore risk shifting during intervention.

According to a second aspect, another object of the present invention is a method for the manufacture of the system for the treatment of a body duct such as described above. According to the invention, this method comprises:

introducing an inflatable expanding element to the interior of a stent forming element, shaped beforehand in the shape desired in the position of use;

inflating said expanding element, such that it comes into contact support on said stent forming element;

folding with a winding of the assembly thus constituted.

According to an actually preferred embodiment of the invention, the above-mentioned folding is carried out radially so as to form round-tipped branches, distributed in a star configuration, said folding being followed by the winding of said branches around the longitudinal axis of the assembly constituted by the stent forming element and the expanding element.

BRIEF DESCRIPTION OF THE DRAWINGS

The invention will be better understood, and other objects, characteristics and advantages thereof will become more clearly apparent, from the following explanatory description referring to the attached schematic drawings, which are given solely by way of non-limiting examples illustrating two currently preferred embodiments of the invention, and in which:

FIG. 1 is a side view which illustrates schematically an assembly for the treatment of a body duct in accordance with the present invention comprising a stent forming element and an inflatable expanding element shown in the folded position;

FIG. 2 is a cutaway view according to line II—II of FIG. 1;

FIG. 3 is a view which is similar to FIG. 1 of the same assembly shown in the position of use after inflation of the balloon;

FIG. 4 is a view similar to FIG. 3 of an assembly comprising a stent forming element according to a second embodiment of the invention;

FIGS. 5, 6 and 7 are partial views in perspective which illustrate the principle of the method for the manufacture of an assembly according to the present invention and which show said assembly in its initial position (FIG. 5), after folding (FIG. 6) and after winding (FIG. 7).

DETAILED DESCRIPTION OF THE PREFERRED EMBODIMENT

An assembly in accordance with the invention has therefore been represented in FIGS. 1, 2 and 3 which is intended for the treatment of a body duct such as a blood vessel in particular a stenotic blood vessel.

This assembly essentially comprises an inflatable expanding element generally designated by the reference number 1, as well as a stent forming element generally designated by the reference number 2.

Generally, the inflatable expanding element 1 which forms the balloon is constituted by a wall of substantially uniform thickness, which defines, in the inflated state, a substantially cylindrical central portion joining together two end portions of generally frustoconical shape.

The inflatable expanding devices have been largely described in the literature to which the person skilled in the art may refer.

The stent forming element 2 comprises a frame made from a material of low elastic recovery capacity, such as, in particular, stainless steel, platinum, gold, tungsten, tantalum, or even a polymer.

In contrast to the stent forming elements used hitherto, the stent forming element of the assembly according to the invention is manufactured and shaped into its shape desired in the active position of use.

In other words, the diameter of this stent forming element will be substantially equal to the normal diameter of the body duct to be treated.

In its actually preferred shape, represented in FIG. 3, the frame of the stent forming element 2 is constituted of a spirally wound wire of non-joined turns which define a substantially cylindrical surface.

Of course, this frame can be of very varied shapes and manufactured for example in the form of a full or perforated fine-walled tube, or even a tube formed from a mesh structure.

In every case, this frame must be manufactured in the shape desired in the use position, and must further be able to be folded with a winding.

The stent forming element can further comprise a cover manufactured in a manner known per se, in a porous, woven, non-woven or expanded polymer, or even an elastic material such as, for example, a polyurethane, which forms a membrane.

This cover can be impregnated or filled with an active principle, intended to be diffused to the site to be treated. Such a cover is for example described in the U.S. Pat. No. 5,383,928 which is incorporated herein by reference.

According to a particular embodiment, the cover and the frame of the stent forming element 2 are connected via attachment points which allow a relative movement of one with respect to the other.

According to another variant, the frame of the stent forming element 2 can be embedded within the cover. To this end, said cover can be manufactured by successive soakings of a mandrel of appropriate shape in a polymer solution, the frame being then disposed between two layers thus prepared.

In the embodiment represented in FIG. 4, the frame of the stent forming element 2 is also constituted of a spirally-wound wire but it comprises an assembly of element portions 3, preferably regularly distributed along the wire, each portion 3 forming a transverse undulation, preferably in the shape of a U, intended for conferring a certain radial expansion capacity to said structure.

As is understood, this shape is advantageous since it confers to the structure of the stent forming element a certain adaptability in radial expansion which guarantees its efficiency.

With reference to FIGS. 5 to 7, the method for the manufacture of the treatment assembly according to the invention will now be described.

As represented in FIG. 5, the inflatable expanding device 1 is introduced into the interior of the stent forming element, in its shape corresponding to the position of use. The expanding device 2 is then inflated, such that it come into contact with at least the frame of the stent forming element 2.

The assembly thus constituted is then folded with a winding around the longitudinal axis L.

More specifically, the assembly is first of all folded radially in order to form branches (3 in the example represented) having rounded ends, distributed in a star configuration in order to obtain the structure represented in FIG. 6.

During this operation, the inflatable expanding device 1 stays in permanent contact with at least the frame of the stent forming element 2. For this, the inflation fluid is left to escape as a function of the pressure applied for forming the folds.

This operation can be done for example, by using a mandrel of appropriate shape such as those usually used for folding balloons and notably those described in the U.S. Pat. No. 5,147,302 which is incorporated herein by reference.

In a third step, the branches 4 formed during the preceding step are wound around the longitudinal axis L of the stent forming element as shown in FIG. 7.

In this shape, the assembly thus constituted has a reduced diameter which enables its introduction into the body duct to be treated. When this assembly is disposed at the site to be treated, the expanding element 1 is then inflated bringing about the regular spreading out of the stent forming element 2.

The system for the treatment of a body duct which has just been described can be positioned in a manner known per se and it is possible in this respect to refer to the documents of the state of the art and in particular to U.S. Pat. No. 4,886,062.

This system will notably be used in the treatment of stenotic blood vessels or even in the treatment of aneurysms.

What is claimed is:

1. An apparatus comprising a stent forming element defining a longitudinal axis and made from a material having a low elastic recovery capacity, said stent forming element capable of restoring and maintaining the cross-section of a body duct to be treated, and an inflatable expanding element disposed within said stent forming element; wherein said stent forming element and said inflatable expanding element are each folded about the longitudinal axis of said stent forming element whereby the apparatus has a size that is sufficient to enable its introduction into the body duct.

2. The apparatus according to claim 1, wherein said stent forming element and said inflatable expanding element are jointly folded to form branches, said branches extending generally parallel to the longitudinal axis and each said branch is bent over in the direction of an adjacent said branch.

3. The apparatus according to claim 1, wherein said stent forming element comprises a frame formed by a spirally-wound wire that, in use, defines a substantially cylindrical surface.

4. The apparatus according to claim 3, wherein said wire comprises a plurality of element portions, each said element portion defined by an undulation in said wire whereby said frame is radially expandable.

5. The apparatus according to claim 4, wherein said undulations are U-shaped.

6. The apparatus according to claim 3, wherein said frame is made from a material selected from stainless steel, platinum, gold, tungsten, tantalum and polymer.

7. The apparatus according to claim 3, wherein said stent forming element further comprises a cover disposed around said frame, and wherein said cover is impregnated with a therapeutic substance.

8. The apparatus according to claim 7, wherein said cover and said frame are connected via attachment points that allow relative movement therebetween.

9. The apparatus according to claim 7, wherein said cover is constructed from a material that is selected from porous, woven, non-woven and expanded polymer, or from an elastic material forming a membrane.

10. The apparatus according to claim 1, wherein said stent forming element comprises a substantially tubular element having a predetermined shape and size that substantially correspond to the shape and size, respectively, of the body duct at the position therein at which the apparatus is to be installed.

11. The apparatus according to claim 1, wherein said stent forming element and said inflatable expanding element are jointly folded.

12. A method for manufacturing an apparatus for the treatment of a body duct, comprising:

a) providing a stent forming element having a longitudinal axis;

b) introducing an inflatable expanding element into an interior of the stent forming element; and c) jointly folding the stent forming element and the inflatable expanding element about the longitudinal axis of the stent forming element.

13. The method according to claim 12, wherein jointly folding the stent forming element and the inflatable expanding element comprises folding the stent forming element and the inflatable expanding element to form a plurality of branches, and thereafter bending each said branch in the direction of an adjacent said branch.

* * * * *